(12) United States Patent
Adams et al.

(10) Patent No.: US 9,498,315 B2
(45) Date of Patent: Nov. 22, 2016

(54) SUB-URETHRAL SLING DELIVERY DEVICE (71) Applicant: Empire Technology Development LLC, Wilmington, DE (US)

(72) Inventors: John Adams, Snohomish, WA (US); Daniel Hawkins, Bellevue, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 150 days.

(21) Appl. No.: 14/031,056

(22) Filed: Sep. 19, 2013

(65) Prior Publication Data

US 2015/0080643 A1   Mar. 19, 2015

(51) Int. Cl.
*A61F 2/00* (2006.01)

(52) U.S. Cl.
CPC ...... *A61F 2/0045* (2013.01); *A61F 2002/0072* (2013.01)

(58) Field of Classification Search
CPC .......... A61B 17/0401; A61B 17/3468; A61B 17/3421; A61B 2017/00805; A61B 2017/00438; A61B 2017/0408; A61F 2/0045
See application file for complete search history.

(56) References Cited

U.S. PATENT DOCUMENTS

| 7,338,432 | B2 | 3/2008 | Valtchev |
| 8,170,686 | B2 | 5/2012 | Moreci et al. |
| 2006/0089524 | A1 | 4/2006 | Chu |
| 2010/0152528 | A1* | 6/2010 | Chapman et al. ............. 600/30 |
| 2010/0256442 | A1* | 10/2010 | Ogdahl et al. ................. 600/30 |

* cited by examiner

*Primary Examiner* — Navin Natnithithadha
*Assistant Examiner* — Kaylee Wilson
(74) *Attorney, Agent, or Firm* — Turk IP Law, LLC (57) ABSTRACT

Technologies are generally provided for a trans-urethral sling delivery device for deploying a sub-urethral sling to support a urethra to treat urinary incontinence. The delivery device may include a conical-shaped cap attached to a distal end of the sling, the cap configured to puncture the urethra to provide access to an area surrounding the urethra. The sling may be wrapped in a reduced profile around a delivery tool having flexible spreading members extending away from each other at an end of the delivery tool. The spreading members may be inserted within the cap, and the device may be inserted through the urethra to deploy the sling. The delivery tool may be gradually removed from urethra, removing the spreading members from the cap, such that the spreading members may expand to spread the sling to a flattened configuration as the spreading members are moved along a length of the sling.

16 Claims, 8 Drawing Sheets

SUB-URETHRAL SLING DELIVERY DEVICE

BACKGROUND

Unless otherwise indicated herein, the materials described in this section are not prior art to the claims in this application and are not admitted to be prior art by inclusion in this section.

Female urinary stress incontinence is a common ailment affecting more than 2 million women annually. Urinary control relies on the finely coordinated activities of the smooth muscle tissue of the urethra and bladder, skeletal muscle, voluntary inhibition, and the autonomic nervous system. Urinary stress incontinence can result from anatomic, physiologic, or pathologic (disease) factors due to aging and childbirth, and can eventually cause inadequate urinary storage or control which may result in bladder leakage. Some effective treatments for incontinence the surgical implantation of device called slings that provide mechanical support for the urethra when pelvic organs shift during points of stress including coughing, sneezing, and laughing, for example. Sling implantation generally involves small skin incisions as well as an incision through the upper vaginal wall to gain appropriate access to position the sling beneath the urethra. Some current sling insertion techniques involve using bulky delivery tools and/or sling containment devices, which can generate significant tissue separation and therefore bleeding to enable implantation. Additionally, the force required on the delivery tool to position the bulky sling devices may cause significant patient discomfort and may require anesthesia.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

According to some examples, the present disclosure describes a delivery device for positioning a sub-urethral sling. The trans-urethral delivery device may include a substantially conical-shaped cap having a hollow center, the cap configured to puncture a wall in one of a urethra and a vagina, a sub-urethral sling attached at one end to the cap, and a flexible delivery tool including at least two flexible spreading members extending from a distal end of the flexible delivery tool, the flexible spreading members configured to be compressed to fit within the hollow center of the cap, wherein the flexible delivery tool may be configured to advance the sub-urethral sling in a reduced delivery profile through the punctured wall of one of the vagina and the urethra and to deploy the sub-urethral sling in a position for supporting the urethra.

According to other examples, the present disclosure also describes a method for delivering a sub-urethral sling. The method may include attaching each end of a sub-urethral sling to a substantially conical-shaped cap having a hollow center, attaching at least two flexible spreading members to a distal end of a flexible delivery tool, wherein the spreading members extend outwards and away from each other in a resting position, pushing the flexible spreading members together into a compressed position and inserting the distal end of the flexible delivery tool including the spreading members in the compressed position into the hollow center of the cap, wrapping the sub-urethral sling in a reduced delivery profile around the flexible delivery tool, encasing the sub-urethral sling and the flexible delivery tool in a protective sheath, advancing the flexible delivery tool including the cap and the sub-urethral sling in the reduced delivery profile encased in the protective sheath through one of a urethra or a vagina such that a wall of the urethra or vagina may be punctured, and advancing a portion of the flexible delivery tool including the cap and the sub-urethral sling in the reduced delivery profile encased in the protective sheath through the puncture such that the distal end of the flexible delivery tool including the cap and the sub-urethral sling extends upwards from the puncture into an interior space near the urethra.

According to further examples, the present disclosure describes a system for deploying a sub-urethral sling. The system may include a sub-urethral sling, wherein a first end and a second end of the sub-urethral sling may be attached to a substantially conical-shaped cap having a hollow center, the conical cap configured to puncture a wall in one of a urethra and a vagina, and a flexible delivery tool including at least two flexible spreading members extending from a distal end of the flexible delivery tool, the flexible spreading members configured be compressed to fit within the hollow center of the cap, wherein the flexible delivery tool may be configured to advance the sub-urethral sling wrapped around a longitudinal axis of the flexible delivery tool in a reduced delivery profile through one of the vagina and the urethra and to deploy the sub-urethral sling in a position for supporting the urethra.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

all arranged in accordance with at least some embodiments as described herein.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to compositions, methods, apparatus, systems, and devices, related to providing a delivery device for positioning a sub-urethral sling.

Briefly stated, technologies are generally provided for a trans-urethral sling delivery device for deploying a sub-urethral sling to support a urethra to treat urinary incontinence. The delivery device may include a conical-shaped cap attached to a distal end of the sling, the cap configured to puncture the urethra to provide access to an area surrounding the urethra. The sling may be wrapped in a reduced profile around a delivery tool having flexible spreading members extending away from each other at an end of the delivery tool. The spreading members may be inserted within the cap, and the device may be inserted through the urethra to deploy the sling. The delivery tool may be gradually removed from urethra, removing the spreading members from the cap, such that the spreading members may expand to spread the sling to a flattened configuration as the spreading members are moved along a length of the sling.

Figure 1:
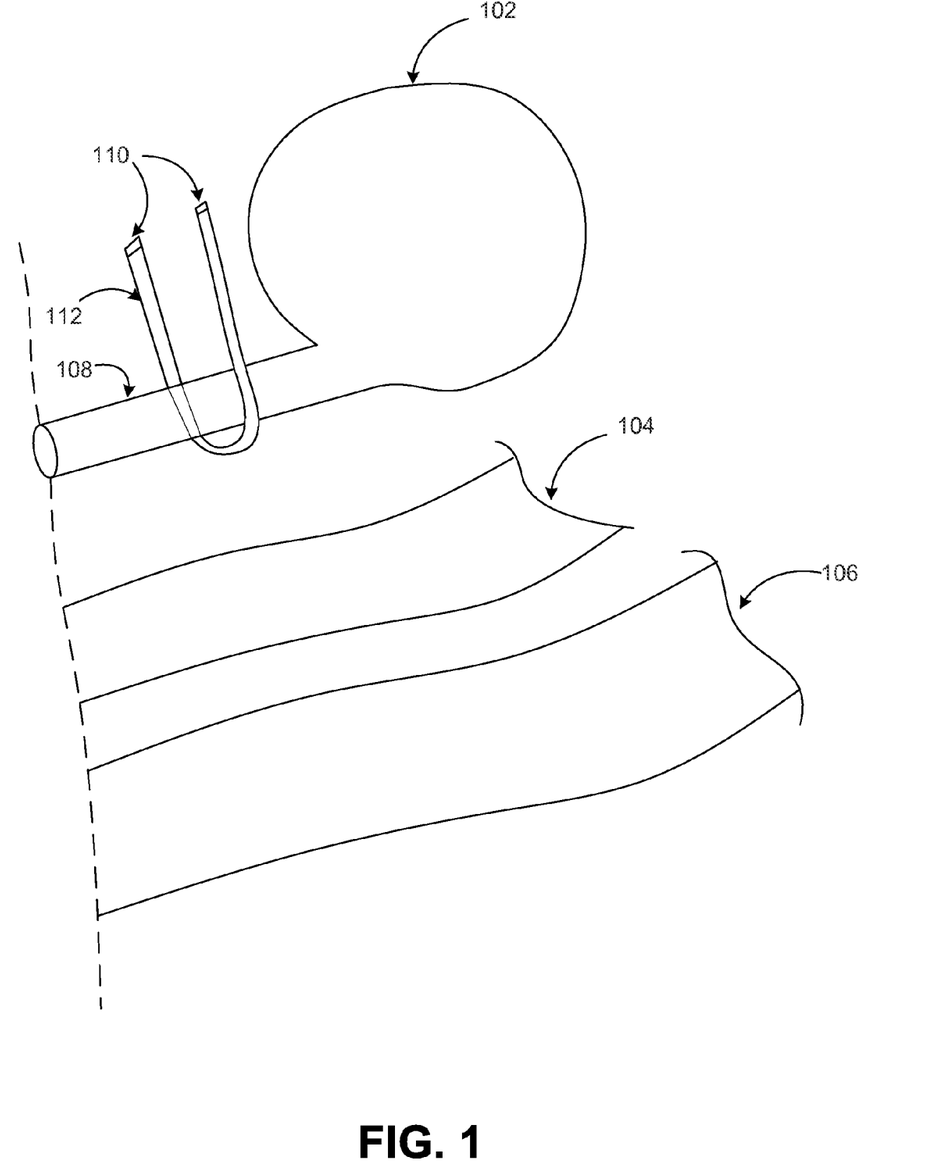
FIG. 1 illustrates an example anatomical layout of the pelvic cavity including the bladder, urethra, vagina, and colon.

FIG. 1 illustrates an example anatomical layout of the pelvic cavity including the bladder, urethra, vagina, and colon, arranged in accordance with at least some embodiments as described herein. The basic pelvic anatomy of a female includes a bladder 102, a vagina 104, and a colon 106. The bladder 102 stores urine, and a urethra 108 is a short narrow tube connected to the bladder 102 that carries the urine from the bladder 102 out of the body. Some females may experience incontinence, which may be the inability to control leakage of bladder. A common solution for helping treat incontinence is the use of a sub-urethral sling 112.

In some embodiments, an example sub-urethral sling 112 may be an elongated mesh ribbon or tape, a middle portion of which may be positioned underneath the urethra 108 for supporting the urethra 108 from beneath. An example sling may have a width in a range from about 1 to about 2 cm. Each end 110 of the sub-urethral sling 112 may be anchored in position above and to either side of the urethra in soft tissue surrounding the bladder for holding the sub-urethral sling 112 in place for supporting the urethra 108 from beneath. When the ends 110 are anchored in the soft tissue, a middle portion of the sub-urethral sling 112 that extends between the two ends 110 may be underneath the urethra 108, and may provide support by holding up the urethra 108.

In an example embodiment, the ends 110 of the sub-urethral sling 112 may be positioned slightly posterior in relation to the middle portion of the sub-urethral sling 112, such that the middle portion of the sub-urethral sling 112 may be positioned at an angle pointing towards the obturator foramen of the pelvic bone. In some example embodiments, the ends 110 of the sub-urethral sling 112 may be positioned through the obturator foramen. The obturator foramen is the hole created by the ischium and pubis bones of the pelvis through which nerves and muscles pass and is located posteriorly in relation to the urethra 108. The ends 110 may be passively or self-anchored in the soft tissue surrounding the bladder and urethra. For example, the ends 110 of the sub-urethral sling 112 may include barbs that enable the ends 110 to embed in the soft tissue naturally without requiring sutures. In other embodiments, the ends 110 may be anchored in place employing sutures or other similar anchoring techniques.

Figure 2:
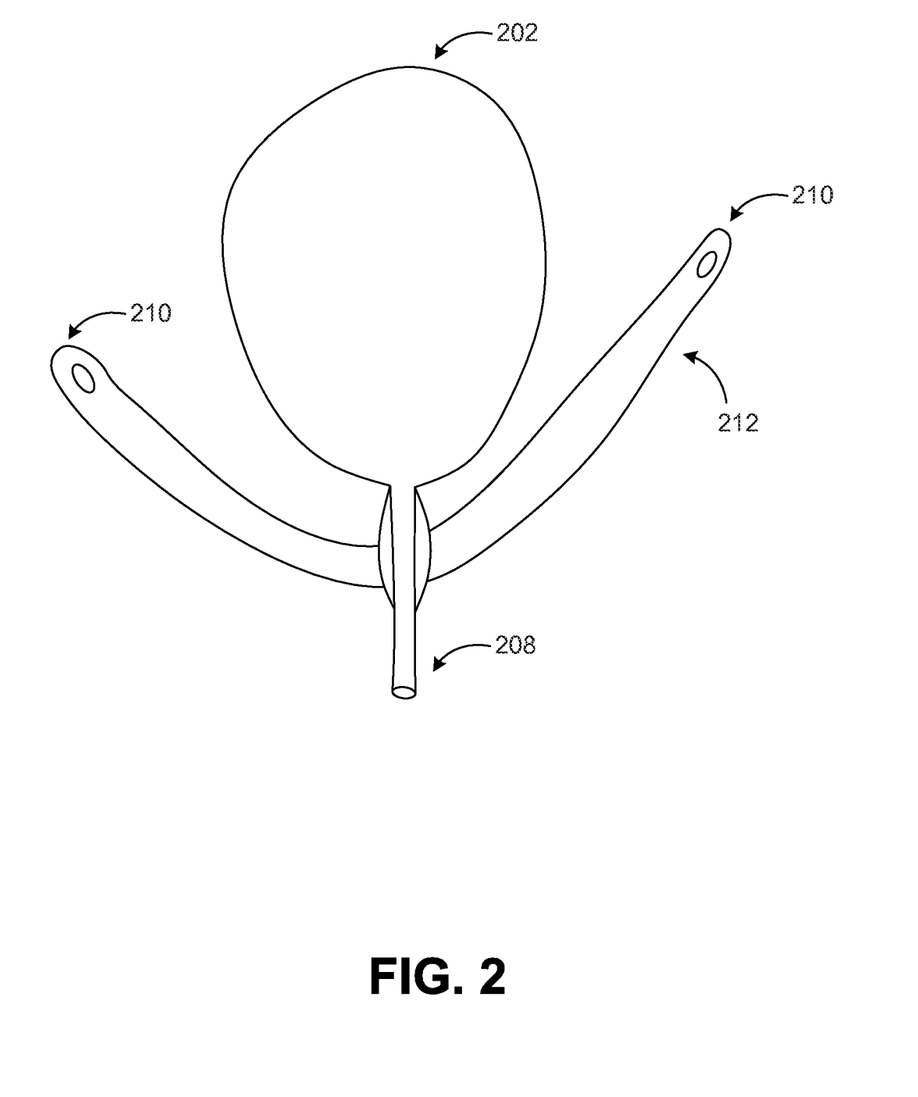
FIG. 2 illustrates an example urethral sling in position for supporting a urethra.

FIG. 2 illustrates an example urethral sling in position for supporting a urethra, arranged in accordance with at least some embodiments as described herein. As previously described, a sub-urethral sling 212 may be an elongated and substantially thin and flat mesh ribbon or tape. The sub-urethral sling 212 may deployed into an expanded position such that a middle portion of the sub-urethral sling 212 may be positioned underneath a urethra 208 for supporting the urethra 208 from beneath. Two ends 210 of the sub-urethral sling 122 may be positioned in the direction of and/or through the obturator foramen, such that the middle portion of the sub-urethral sling 212 is positioned an angle pointing towards the obturator foramen of the pelvic bone.

In a system according to embodiments, the sub-urethral sling 212 may be delivered and positioned employing minimally invasive surgery techniques in order to reduce risks, bleeding, recovery time, and pain for the patient. In order for the sub-urethral sling 212 to be inserted into the body and deployed to the expanded position, the sub-urethral sling 212 may be initially configured in a reduced delivery profile, or a more compact configuration, for enabling the sub-urethral sling 212 to be delivered through a minimally invasive technique. Once the sub-urethral sling 212 is delivered employing a minimally invasive technique as described herein, the sub-urethral sling 212 may be deployed into the expanded position such that the ends 210 may be anchored in a position in soft tissue surrounding the bladder 202 and urethra 208 for enabling the middle portion of the sub-urethral sling 212 to provide support to the urethra 208 from beneath.

Figure 3:
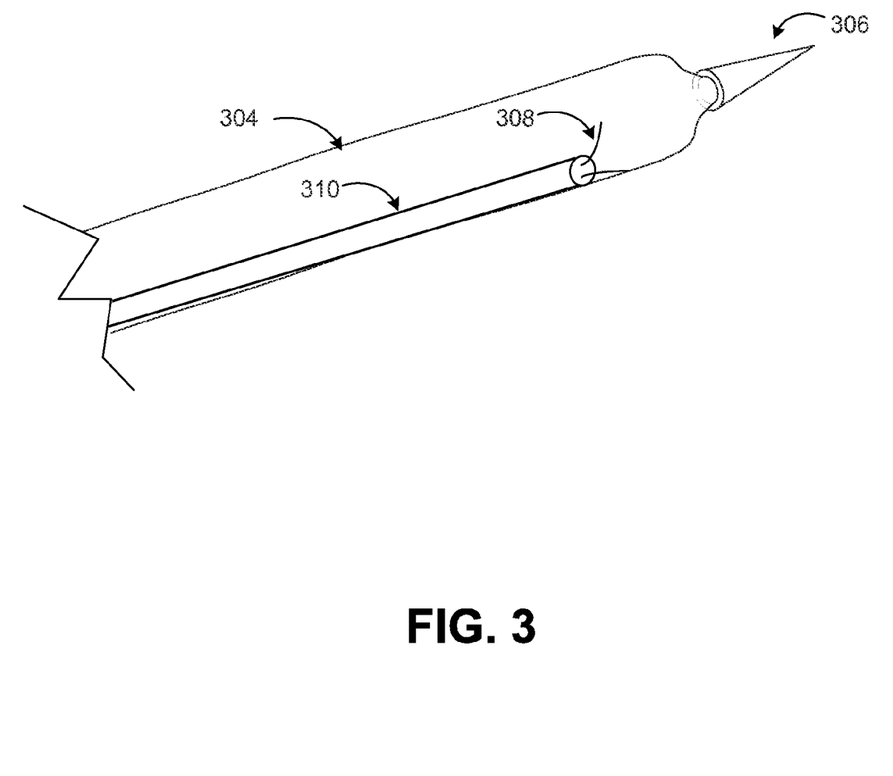
FIG. 3 illustrates an example sub-urethral sling attached to a cap and a delivery tool with spreading members.

FIG. 3 illustrates an example sub-urethral sling attached to a cap and a delivery tool with spreading members, according to at least some embodiments as described herein. As previously described, it may be desirable to employ a minimally invasive procedure to insert and deploy a sub-urethral sling 304 in a position for supporting a urethra.

In a system according to embodiments a trans-urethral sling delivery device may be advanced through a urethra for inserting and deploying the sub-urethral sling 304 in a position for supporting the urethra. The trans-urethral sling delivery device may include a substantially conical-shaped cap 306 attached to a distal end of the sub-urethral sling 304. The cap 306 may be configured to puncture a urethral wall to provide access to the interior area of the pelvic area surrounding the urethra and the bladder. The trans-urethral sling delivery device may also include a delivery tool 310 that may be coupled with the sub-urethral sling 304 and attached conical shaped cap 306 to advance the sub-urethral sling through the urethra and to deploy the sub-urethral sling 204 in position in the soft tissue surrounding the bladder and urethra.

In an example embodiment, the delivery tool 310 may include at least two flexible spreading members 308 extending from a distal end of the flexible delivery tool 310. The flexible spreading members 308 may be configured to be compressed to fit within a hollow center of the cap 306 such that the flexible delivery tool 310 may be inserted within the cap 306 to facilitate guiding the sub-urethral sling 304 and attached cap 306.

In an example scenario for deploying the sub-urethral sling 304 in a minimally invasive manner, after inserting the delivery tool within the hollow cap 306, the sub-urethral sling 304 may be wrapped around the delivery tool 310 along a longitudinal axis of the delivery tool 310 such that the sub-urethral sling is configured in a reduced delivery profile. The delivery tool 310 including the including the cap 306 and the sub-urethral sling 304 in the reduced delivery profile may be advanced through the puncture in the urethral wall such that the distal end of the delivery tool 310 including the cap 306 and the sub-urethral sling 304 may extend upwards from the puncture into an interior space near the urethra.

The delivery tool 310 may be composed from a flexible polymer material to enable the delivery tool 310 to freely bend and straighten as the delivery tool 310 is advanced through the urethra. The distal end of the delivery tool 310 may be bent into a curved position such that a curved portion of the delivery tool may extend from the punctured urethral wall to deploy the cap 306 and sling 304 in a desired position. The delivery tool 310 may have a diameter in a range from about 4 mm to about 5 mm for maintaining a reduced profile of the delivery tool in order to enable the flexible tool to fit within the urethra while minimizing trauma to the urethra, vagina and surrounding tissue.

In another embodiment as will be described in further detail, a tube or cannula may be advanced through one of the urethra or the vagina to enable the passage of the delivery tool 310 including the sub-urethral sling 304 and cap 306. The tube may be configured to puncture a wall of the urethra or vagina, and the tube may be bent such that a curved portion of the tube extends upwards from the puncture in the urethra or vagina. The delivery tool 310 including the cap 306 and the sub-urethral sling 304 may be advanced through the tube such that the distal end of the delivery tool 310 may extend out of a distal end of the tube into the interior space near the urethra.

Figure 4:
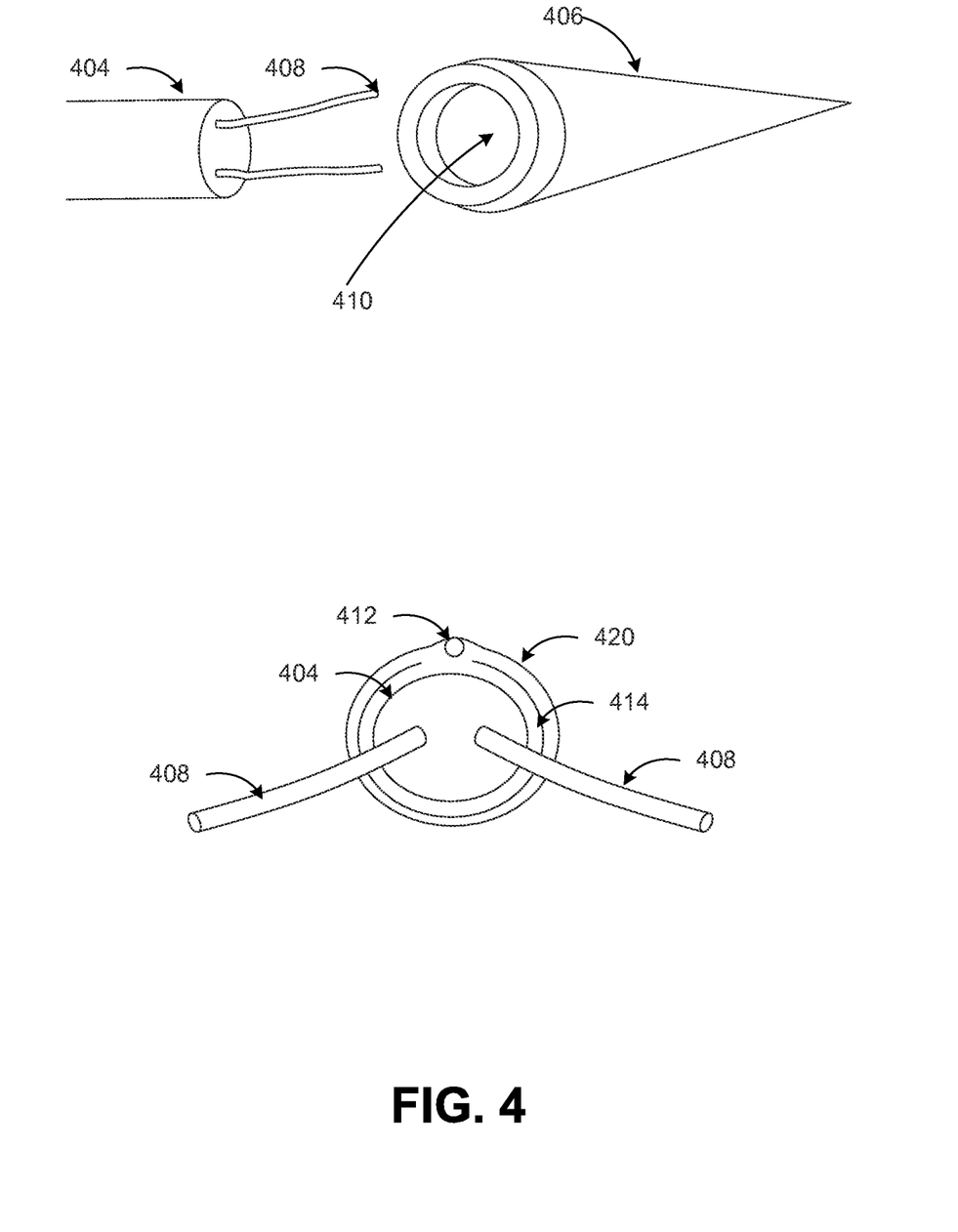
FIG. 4 illustrates an example conical shaped cap and a delivery tool including spreading members.

FIG. 4 illustrates an example conical shaped cap and a delivery tool including spreading members, according to at least some embodiments as described herein. As described above in conjunction with FIG. 3, a sling delivery device may include a sub-urethral sling 414 attached at a distal end to a substantially conical shaped cap 406. The sling delivery device may also include a delivery tool 404 including at least two flexible spreading members 408 attached at a distal end of the delivery tool 404. The flexible spreading members 408 may be configured to facilitate unwrapping the sub-urethral sling 414 from the delivery tool to deploy the sub-urethral sling 414 into a flattened configuration for supporting the urethra.

In a system according to embodiments, the flexible spreading members 408 may be configured to extend outwards and away from each other in a default or resting position. The spreading members 408 may also be pushed together into a compressed position to fit within a hollow center 410 of the cap 406 such that the delivery tool 404 may be coupled with the cap 406 to guide the sling and attached cap 406. When the spreading members 408 are removed from the cap 406, the spreading members may be configured to naturally return to the resting position to facilitate spreading the sub-urethral sling into an expanded flattened configuration.

In an example embodiment, as previously described, the sub-urethral sling 414, the sub-urethral sling 414 may be wrapped around the delivery tool 404 in a reduced delivery profile. Additionally, a protective sheath 420 may be wrapped around the delivery tool 404 and the sub-urethral sling 414 to encase the sub-urethral sling 414 for advancement through the urethra or vagina. The protective sheath 420 may include a tear cord 412 along a length of the protective sheath 420 to enable the protective sheath 420 to be longitudinally tear-opened to expose the sub-urethral sling 414 when the tear cord 412 is pulled.

Figure 5:
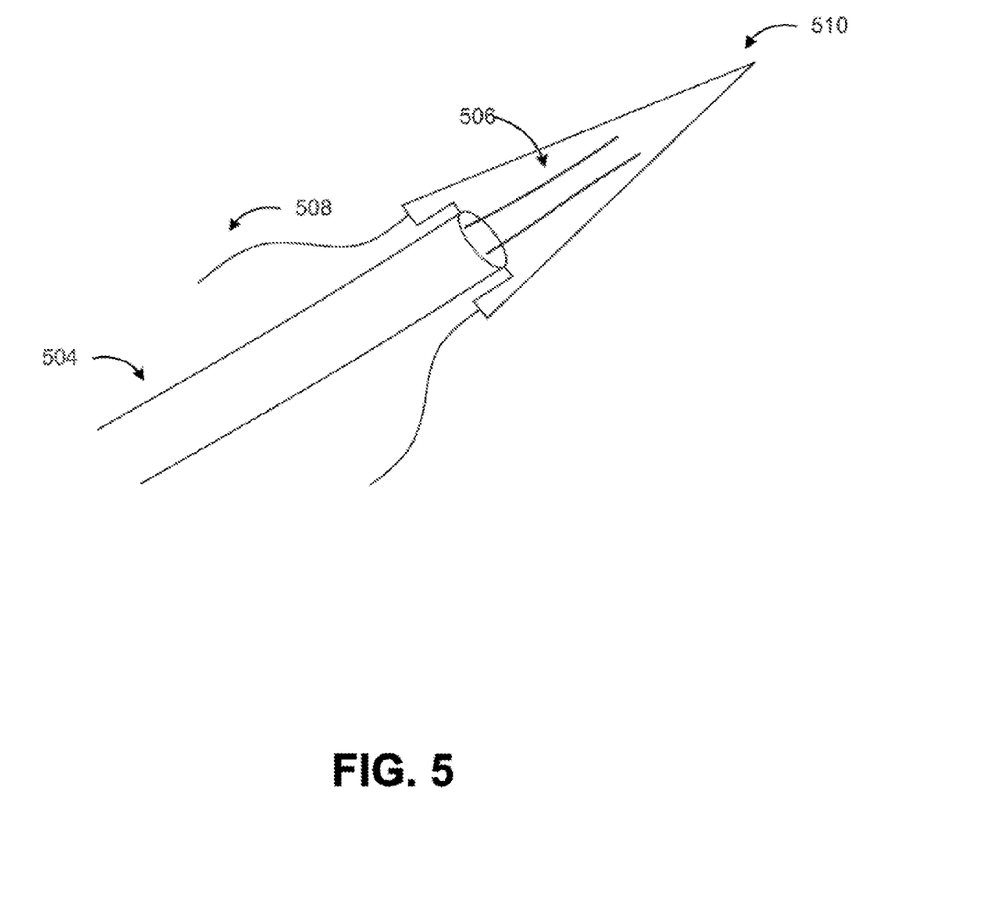
FIG. 5 illustrates an example delivery tool including spreading members inserted within a cap of a sub-urethral sling.

FIG. 5 illustrates an example delivery tool including spreading members inserted within a cap of a sub-urethral sling, according to at least some embodiments as described herein. Flexible spreading members 506 extending from a distal tip of a delivery tool 504 may be configured to extend away from each other in a resting position. The spreading members 506 may be pushed together into a compressed position to fit within a hollow center of the cap 510, such that the delivery tool 504 may be coupled with the cap 510 to guide and deploy the sub-urethral sling 508 and attached cap 510. Example spreading members may be composed from a wire or a polymer material such that they may be configured to naturally tend toward an initial configuration extending outward and away from each other.

Figure 6:
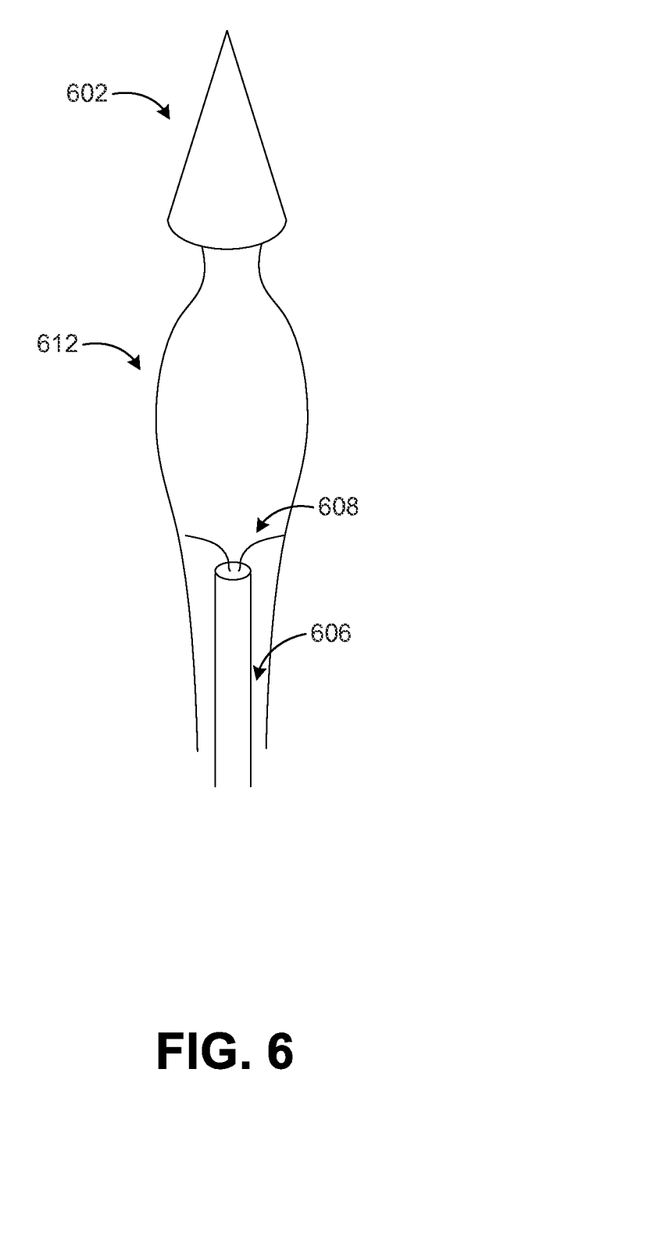
FIG. 6 illustrates flattening the sub-urethral sling with the spreading members by removing the delivery tool.

FIG. 6 illustrates flattening the sub-urethral sling with the spreading members by removing the delivery tool, according to at least some embodiments as described herein. As described in conjunction with FIG. 5, two or more spreading members 608 extending from a distal end of a delivery tool 606 may be pushed together and inserted with a hollow center of a cap 602 attached to a sub-urethral sling 612 to help guide and deploy the sub-urethral sling 612. The sub-urethral sling 612 may be initially wrapped around the delivery tool 606 in a reduced profile for advancement through the urethra. After the sub-urethral sling 612 is inserted into a desired position, the delivery tool 606 may be gradually pulled out of the urethra, thereby removing the spreading members 608 from the cap 602, and enabling the spreading members 608 to naturally extend into their resting position. When the spreading members 408 are in the resting position, the spreading members 608 may expand the sub-urethral sling 612 from the reduced delivery profile around the flexible delivery tool 606 to an expanded flattened configuration as the flexible delivery tool 606 is pulled out of one of the urethra. Additionally, the spreading members 408 may dissect tissue surrounding the urethra to enable the sub-urethral sling 612 to expand into the expanded flattened configuration as the delivery tool 606 is pulled out of one of the urethra.

Figure 7:
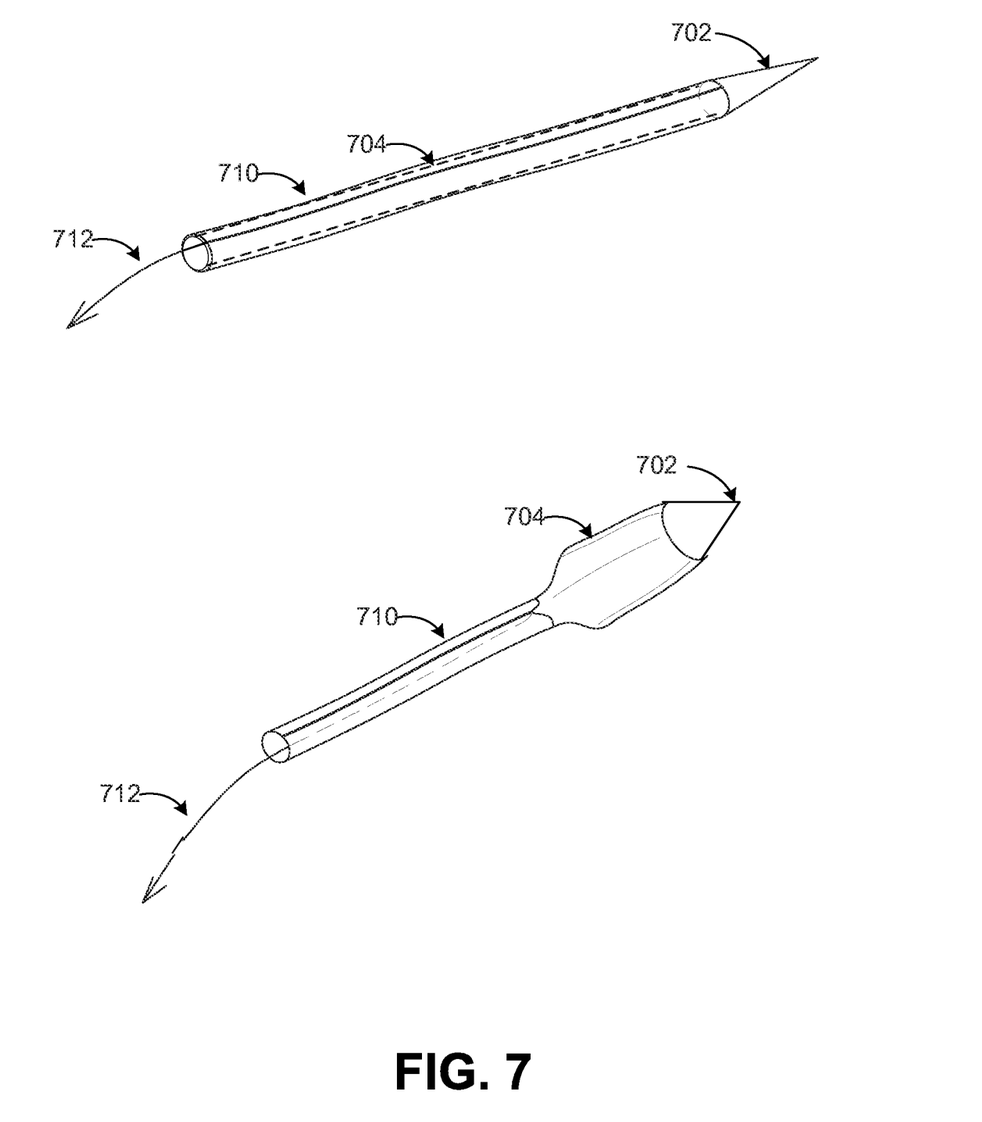
FIG. 7 illustrates a sub-urethral sling in a reduced delivery profile around a delivery tool encased in a protective sheath.

FIG. 7 illustrates a sub-urethral sling in a reduced delivery profile around a delivery tool encased in a protective sheath, according to at least some embodiments as described herein. An example sub-urethral sling 704 may be wrapped around a delivery tool along a longitudinal axis of the delivery tool such that the sub-urethral sling may be configured in a reduced delivery profile.

A protective sheath 710 may be wrapped around the delivery tool and the sub-urethral sling 704 to encase and protect the sub-urethral sling 704. The protective sheath 710 may include a tear cord 712 along a length of the protective sheath 710 to enable the protective sheath 710 to be longitudinally tear-opened to expose the sub-urethral sling 704 when the tear cord 712 is pulled.

In an example scenario for deploying the sub-urethral sling 704 in position to support the urethra, the flexible delivery tool including the wrapped sub-urethral sling 704 and attached conical shaped cap 702 may be encased in the protective sheath 710 and advanced through a punctured urethral wall into a position surrounding the urethra. When the distal end of the delivery tool extends into the interior space near the urethra, the protective sheath 710 may be removed by pulling the tear cord 712 to expose the sub-urethral sling 704. The delivery tool may be gradually removed from the cap 702 attached at the distal end of the sub-urethral sling 704 to pull the spreading members from the inside of the cap 702. When the spreading members are removed from the inside of the cap 702, the spreading members may extend from a compressed position to a resting position. The spreading members may expand the sub-urethral sling from the wrapped reduced profile configuration to a flattened configuration as the delivery tool is gradually removed and the spreading members are moved along a length of the sub-urethral sling. The process may be repeated on each end of the sub-urethral sling to deploy the sling such that each end of the sub-urethral sling 704 may be anchored in on either side of the urethra and a middle portion of the sub-urethral sling that extends between the two ends may be underneath the urethra to provide support by holding up the urethra from beneath.

Figure 8:
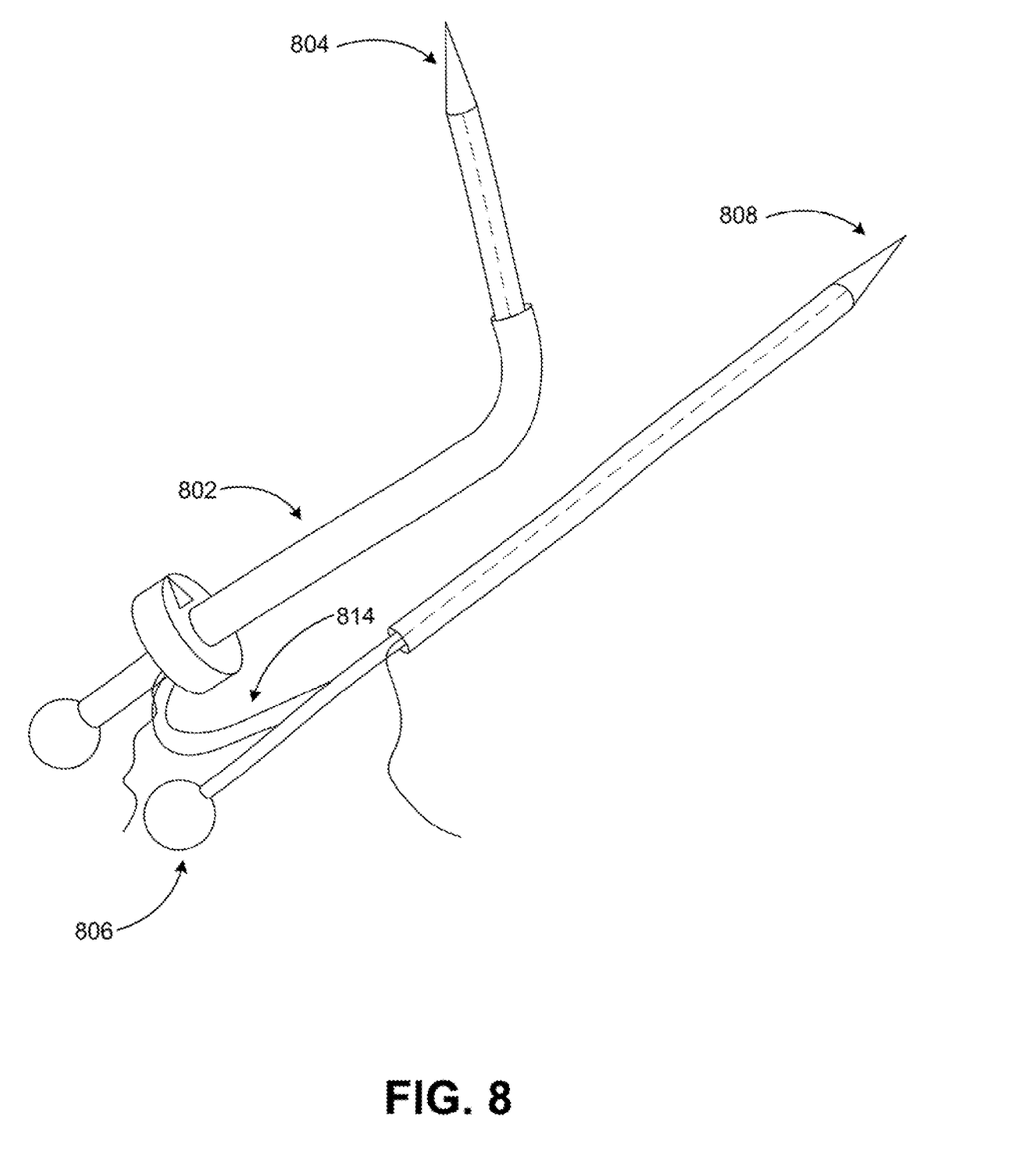
FIG. 8 illustrates delivery of the sub-urethral sling employing a tube.

FIG. 8 illustrates delivery of the sub-urethral sling employing a tube, according to at least some embodiments as described herein. In an additional embodiment, a tube 802 or cannula may be advanced through one of the urethra or the vagina to facilitate the passage of the delivery tool 806 including the sub-urethral sling 814 and cap. The tube 802 may be configured to puncture a wall of the urethra or vagina, and the tube 802 may pass through the puncture into an interior space surrounding the urethra and the bladder. Alternatively, the delivery tool 806 may be advanced through the tube 802 and cap attached to the sub-urethral sling 814 may be employed to puncture the urethral wall. The tube 802 and the delivery tool 806 including the cap and sub-urethral sling 814 may pass through the puncture. In another embodiment, a surgical tool may be advanced through the tube 802 to puncture the urethral wall, and the tube 802 may be advanced through the puncture.

In an example embodiment, the tube 802 may be configured to be bent such that a curved portion of the tube may extend upwards from the puncture in the urethral wall. The delivery tool 806 including the cap and the sub-urethral sling 814 may be advanced through the tube 802 such that the distal end of the delivery tool including the cap may extend out of the tube into the interior space near the urethra.

When the delivery tool 806 extends into the interior space surrounding the urethra, the sub-urethral sling 814 may be deployed into position as previously described to anchor the sub-urethral sling 814 such that a first end 804 of the sub-urethral sling 814 may be anchored in soft tissue on one side of the urethra, a middle portion of the sub-urethral sling 814 extending between the first end and a second end 808 of the sub-urethral sling 814 may be positioned underneath the urethra, and the second end of the sub-urethral sling 814 may be anchored in soft tissue on the other side of the urethra.

In an example scenario for deploying the sub-urethral sling 814, once the tube 802 has been advanced through the puncture in the urethra, the first end 804 of the sub-urethral sling 814 including a conical shaped cap may be coupled with the flexible delivery tool as previously described in conjunction with FIG. 7 such that spreading members on the delivery tool may be compressed to fit within a hollow interior of the conical shaped cap. The flexible delivery tool along with the attached first end 804 of the sub-urethral sling and cap may be advanced through the tube 802. The flexible delivery tool may deliver the attached first end 804 of the sub-urethral sling to a desired position near the urethra and the bladder, and may anchor the first end in place. A protective sheath may be removed to expose the sub-urethral sling, and the flexible delivery tool may then be gradually removed from the tube 802 and the urethra. As the flexible delivery tool is removed, the spreading members may be removed from the cap and may return to their expanded resting position to spread the sub-urethral sling 814 into the flattened configuration.

Subsequently, the second end 808 of the sub-urethral sling 814 including a second conical shaped cap may be coupled with the flexible delivery tool, and the spreading members on the end of the flexible delivery tool may be compressed and inserted within the second conical shaped cap. The tube 802 may be rotated to the other side of the urethra, and the flexible delivery tool 806 along with the attached second end 808 of the sub-urethral sling and cap may be advanced through the tube 802. The flexible delivery tool may deliver the attached second end 808 of the sub-urethral sling 814 to a desired position near the urethra and the bladder, and may anchor the second end 808 in place. The protective sheath may be removed to expose the sub-urethral sling 814, and the flexible delivery tool may then be gradually removed from the delivery, enabling the spreading members to return to the expanded resting position for spreading the sub-urethral sling 814 into the flattened configuration. After both ends of the sub-urethral sling have been delivered and positioned in soft tissue in a desired position near the urethra and the bladder, the tube 802 may be removed from the urethra.

In an example embodiment, the conical shaped cap may be configured to remain inside the body with the sub-urethral sling. Additionally, the conical shaped cap may be employed as anchors for anchoring the sling in position in the soft tissue. The cap may be composed from a bio-absorbable material such that the cap may be absorbed by the body over time. The cap may alternatively be composed from a biocompatible material such that the cap may remain with the sub-urethral sling inside the body.

While embodiments have been discussed above using specific examples, components, and configurations, they are intended to provide a general guideline to be used for a trans-urethral sling delivery device for deploying a sub-urethral sling to support a urethra to treat urinary incontinence. While the sling delivery device has been described as a trans-urethral device, the device may be delivered through the vagina and similarly deployed by puncturing a wall of the vagina to position the sub-urethral sling in position to support the urethra. These examples do not constitute a limitation on the embodiments, which may be implemented using other components, modules, and configurations using the principles described herein. Furthermore, actions discussed above may be performed in various orders, especially in an interlaced fashion.

According to some examples, the present disclosure describes a delivery device for positioning a sub-urethral sling. The trans-urethral delivery device may include a substantially conical-shaped cap having a hollow center, the cap configured to puncture a wall in one of a urethra and a vagina, a sub-urethral sling attached at one end to the cap, and a flexible delivery tool including at least two flexible spreading members extending from a distal end of the flexible delivery tool, the flexible spreading members configured to be compressed to fit within the hollow center of the cap, wherein the flexible delivery tool may be configured to advance the sub-urethral sling in a reduced delivery profile through the punctured wall of one of the vagina and the urethra and to deploy the sub-urethral sling in a position for supporting the urethra.

According to some examples, the flexible delivery tool may be configured to advance through the puncture in the wall of one of the urethra or the vagina such that the distal end of the flexible delivery tool including the cap and the sub-urethral sling extends upwards from the puncture into an interior space near the urethra.

According to some examples, the device may also include a tube configured to fit over the flexible delivery tool and the sub-urethral sling and configured to be bent into a curved position such that a curved portion of the tube extends upwards from the puncture and the distal end of the flexible delivery tool extends out of an end of the tube into an interior space near the urethra.

According to some examples, the sub-urethral sling may be configured to be wrapped around the flexible delivery tool along a longitudinal axis of the flexible delivery tool in the reduced delivery profile, and wherein a protective sheath may be wrapped around the sub-urethral sling and the flexible delivery tool to encase the sub-urethral sling for advancement through the puncture. The flexible spreading members may be configured to extend away from each other in a resting position for spreading the sub-urethral sling into an expanded flattened configuration.

According to some examples, the flexible spreading members may be configured to return to the resting position for spreading the sub-urethral sling into the flattened configuration when the flexible delivery tool may be removed from the cap. The flexible spreading members in the resting position may be configured to expand the sub-urethral sling from the reduced delivery profile around the flexible delivery tool to the expanded flattened configuration as the flexible delivery tool may be pulled out of one of the vagina or the urethra.

According to some examples, in the expanded flattened configuration, a first end of the sub-urethral sling may be anchored in soft tissue on one of a left side and a right side of the urethra, a middle portion of the sub-urethral sling extending between the first end and a second end of the sub-urethral sling may be positioned underneath the urethra, and the second end of the sub-urethral sling may be anchored in soft tissue on the other of the left side and the right side of the urethra, such that the sub-urethral sling supports the urethra from beneath.

According to other examples, the present disclosure also describes a method for delivering a sub-urethral sling. The method may include attaching each end of a sub-urethral sling to a substantially conical-shaped cap having a hollow center, attaching at least two flexible spreading members to a distal end of a flexible delivery tool, wherein the spreading members extend outwards and away from each other in a resting position, pushing the flexible spreading members together into a compressed position and inserting the distal end of the flexible delivery tool including the spreading members in the compressed position into the hollow center of the cap, wrapping the sub-urethral sling in a reduced delivery profile around the flexible delivery tool, encasing the sub-urethral sling and the flexible delivery tool in a protective sheath, advancing the flexible delivery tool including the cap and the sub-urethral sling in the reduced delivery profile encased in the protective sheath through one of a urethra or a vagina such that a wall of the urethra or vagina may be punctured, and advancing a portion of the flexible delivery tool including the cap and the sub-urethral sling in the reduced delivery profile encased in the protective sheath through the puncture such that the distal end of the flexible delivery tool including the cap and the sub-urethral sling extends upwards from the puncture into an interior space near the urethra.

According to some examples, the method may also include pulling a tear cord integrated along a length of the protective sheath to longitudinally tear open the protective sheath and to expose the sub-urethral sling, and removing the protective sheath from one of the urethra or vagina. The method may also include gradually pulling the flexible delivery tool from the urethra or the vagina to remove the distal end of the flexible delivery tool including the flexible spreading members from the cap such that the flexible spreading members expand from the compressed position into the resting position extending away from each other, wherein the flexible spreading members in the resting position may be configured to dissect tissue surrounding the urethra and to expand the sub-urethral sling from the reduced delivery profile around the flexible delivery tool to an expanded flattened configuration as the flexible delivery tool may be pulled out of one of the vagina or the urethra.

According to some examples, the method may also include advancing a tube through one of the urethra and the vagina configured to puncture a wall of the urethra and vagina, such that a curved portion of the tube extends upwards from the puncture in the urethra or vagina, and advancing the flexible delivery tool including the cap and sub-urethral sling in the reduced delivery profile through the tube such that the distal end of the flexible delivery tool extends out of an end of the tube into the interior space near the urethra.

According to further examples, the present disclosure describes a system for deploying a sub-urethral sling. The system may include a sub-urethral sling, wherein a first end and a second end of the sub-urethral sling may be attached to a substantially conical-shaped cap having a hollow center, the conical cap configured to puncture a wall in one of a urethra and a vagina, and a flexible delivery tool including at least two flexible spreading members extending from a distal end of the flexible delivery tool, the flexible spreading members configured be compressed to fit within the hollow center of the cap, wherein the flexible delivery tool may be configured to advance the sub-urethral sling wrapped around a longitudinal axis of the flexible delivery tool in a reduced delivery profile through one of the vagina and the urethra and to deploy the sub-urethral sling in a position for supporting the urethra.

According to some examples, the flexible delivery tool may be configured to advance through the puncture in the wall of one of the urethra or the vagina such that the distal end of the flexible delivery tool including the cap and the sub-urethral sling extends upwards from the puncture into an interior space near the urethra.

According to some examples, the system may also include a protective sheath wrapped around the sub-urethral sling and the flexible delivery tool to encase the sub-urethral sling for advancement through the puncture, wherein the protective sheath includes a tear cord along a length of the protective sheath for enabling the protective sheath to be longitudinally tear-opened and to expose the sub-urethral sling when the tear cord may be pulled.

According to other examples, the flexible spreading members may be configured to extend away from each other in a resting position, and may be configured to be pushed together into a compressed position to fit within the hollow center of the cap. The flexible delivery tool may be pulled out of one of the vagina or the urethra to remove the flexible delivery tool from the cap.

According to other examples, the cap may be configured to remain inside the body attached to the sub-urethral sling after removal of the flexible delivery tool. The flexible spreading members may be configured to return to the resting position for spreading the sub-urethral sling into an expanded flattened configuration when the flexible delivery tool may be removed from the cap.

According to further examples, in the expanded flattened configuration, a first end of the sub-urethral sling may be anchored in soft tissue on one of a left side and a right side of the urethra, a middle portion extending between the first end and a second end of the sub-urethral sling may be positioned underneath the urethra, and the second end of the sub-urethral sling may be anchored in soft tissue on the other of the left side and the right side of the urethra, such that the sub-urethral sling supports the urethra from beneath.

According to further examples, the flexible delivery tool may be composed from one or more of: a polymer. The flexible spreading members may be composed from one or more of: a wire or a polymer material. The cap may be composed from one or more of: a polymer and a bio-absorbable material.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected," or "operably coupled," to each other to achieve the desired functionality, and any two components capable of being so associated may also be viewed as being "operably couplable," to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A sub-urethral sling delivery device, the delivery device comprising:
    a substantially conical-shaped cap having a hollow center, the cap configured to puncture a wall in one of a urethra and a vagina when the delivery device is advanced through the wall in one of the urethra and the vagina;
    a sub-urethral sling attached at one end to the cap and configured to support a urethra from beneath; and
    a flexible delivery tool configured to enable the sub-urethral sling to be wrapped around the flexible delivery tool along a longitudinal axis of the delivery tool in a reduced delivery profile, wherein
        a longitudinal axis of the sub-urethral sling is aligned with the longitudinal axis of the flexible delivery tool when the sub-urethral sling is wrapped around the flexible delivery tool,
        the flexible delivery tool includes at least two flexible spreading members extending from a distal end of the flexible delivery tool, the flexible spreading members configured to be pushed into a compressed position to fit within the hollow center of the cap,
        the flexible delivery tool is configured to advance the sub-urethral sling in the reduced delivery profile through the punctured wall of one of the vagina and the urethra such that the distal end of the flexible delivery tool including the cap and the sub-urethral sling extend upwards from the puncture into an interior space near the urethra and deploy the sub-urethral sling in a position to support the urethra, and
        the flexible spreading members are further configured to return to a resting position for spreading the sub-urethral sling into a flattened configuration when the flexible delivery tool is removed from the cap, wherein in the resting position the flexible spreading members naturally tend towards an outward extending configuration in which the flexible spreading members extend away from each other.

2. The delivery device of claim 1, further comprising:
    a tube configured to fit over the flexible delivery tool and the sub-urethral sling and configured to be bent into a curved position such that a curved portion of the tube extends upwards from the puncture and the distal end of the flexible delivery tool extends out of an end of the tube into an interior space near the urethra.

3. The delivery device of claim 1, wherein a protective sheath is wrapped around the sub-urethral sling and the flexible delivery tool to encase the sub-urethral sling for advancement through the puncture.

4. The delivery device of claim 1, wherein the flexible members in the resting position are configured to expand the sub-urethral sling from the reduced delivery profile around the flexible delivery tool to the expanded flattened configuration as the flexible delivery tool is pulled out of one of the vagina or the urethra.

5. The delivery device of claim 4, wherein in the expanded flattened configuration, a first end of the sub-urethral sling is anchored in soft tissue on one of a left side and a right side of the urethra, a middle portion of the sub-urethral sling extending between the first end and a second end of the sub-urethral sling is positioned underneath the urethra, and the second end of the sub-urethral sling is anchored in soft tissue on the other of the left side and the right side of the urethra, such that the sub-urethral sling supports the urethra from beneath.

6. A method for delivering a sub-urethral sling, the method comprising:
    attaching an end of a sub-urethral sling to a substantially conical-shaped cap of a flexible delivery tool, the cap having a hollow center;
    wrapping the sub-urethral sling in a reduced delivery profile around the flexible delivery tool such that a longitudinal axis of the sub-urethra sling is aligned with the longitudinal axis of the flexible delivery tool when the sub-urethral sling is wrapped around the flexible delivery tool;
    encasing the sub-urethral sling and the flexible delivery tool in a protective sheath;
    attaching at least two flexible spreading members to a distal end of the flexible delivery tool, wherein the spreading members naturally extend outwards and away from each other in a resting position; pushing the flexible spreading members together into a compressed position and inserting the distal end of the flexible delivery tool including the spreading members in the compressed position into the hollow center of the cap;
    advancing the flexible delivery tool including the cap and the sub-urethral sling in the reduced delivery profile encased in the protective sheath through one of a urethra or a vagina such that a wall of the urethra or vagina is punctured and the distal end of the flexible delivery tool including the cap and the sub-urethral sling extends upwards from the puncture into an interior space near the urethra; and
    gradually pulling the flexible delivery tool from the urethra or the vagina to remove the distal end of the flexible delivery tool including the flexible spreading members from the cap such that the flexible spreading members expand from the compressed position into the resting position extending away from each other, wherein the flexible spreading members in the resting position are configured to expand the sub-urethral sling from the reduced delivery profile around the flexible delivery tool to an expanded flattened configuration as the flexible delivery tool is pulled out of one of the vagina or the urethra.

7. The method of claim 6, wherein the flexible spreading members in the resting position are configured to dissect tissue surrounding the urethra.

8. The method of claim 6, further comprising:
    pulling a tear cord integrated along a length of the protective sheath to longitudinally tear open the protective sheath and to expose the sub-urethral sling; and
    removing the protective sheath from one of the urethra or vagina.

9. A system to deploy a sub-urethral sling, comprising:
    a sub-urethral sling, wherein a first end and a second end of the sub-urethral sling are attached to a substantially conical-shaped cap having a hollow center, the conical cap configured to puncture a wall in one of a urethra and a vagina; and a flexible delivery tool configured to:
- advance through the puncture in the wall of one of the urethra or the vagina such that the distal end of the flexible delivery tool including the cap and the sub-urethral sling extend upwards from the puncture into an interior space near the urethra;
- advance the sub-urethral sling wrapped around a longitudinal axis of the flexible delivery tool in a reduced delivery profile through one of the vagina and the urethra, wherein a longitudinal axis of the sub-urethral sling is aligned with the longitudinal axis of the flexible delivery tool when the sub-urethral sling is wrapped around the flexible delivery tool; and
- deploy the sub-urethral sling in a position to support the urethra, wherein the flexible delivery tool includes at least two flexible spreading members extending from a distal end of the flexible delivery tool, the flexible spreading members configured to be pushed into a compressed position to fit within the hollow center of the cap and to return to a resting position for spreading the sub-urethral sling into a flattened configuration when the flexible delivery tool is removed from the cap, wherein in the resting position the flexible spreading members naturally tend toward an outward extending configuration in which the flexible spreading members extend away from each other.

10. The system of claim 9, further comprising:
a protective sheath wrapped around the sub-urethral sling and the flexible delivery tool to encase the sub-urethral sling for advancement through the puncture, wherein the protective sheath includes a tear cord along a length of the protective sheath for enabling the protective sheath to be longitudinally tear-opened and to expose the sub-urethral sling when the tear cord is pulled.

11. The system of claim 9, wherein the flexible delivery tool is pulled out of one of the vagina or the urethra to remove the flexible delivery tool from the cap.

12. The system of claim 11, wherein the cap is configured to remain inside the body attached to the sling after removal of the flexible delivery tool.

13. The system of claim 9, wherein in the expanded flattened configuration, a first end of the sub-urethral sling is anchored in soft tissue on one of a left side and a right side of the urethra, a middle portion extending between the first end and a second end of the sub-urethral sling is positioned underneath the urethra, and the second end of the sub-urethral sting is anchored in soft tissue on the other of the left side and the right side of the urethra, such that the sub-urethral sling supports the urethra from beneath.

14. The system of claim 9, wherein the flexible delivery tool is composed from a polymer.

15. The system of claim 9, wherein the flexible spreading members are composed from one or more of: a wire or a polymer material.

16. The system of claim 9, wherein the cap is composed from one or more of:
a polymer and a bio-absorbable material.

* * * * *

UNITED STATES PATENT AND TRADEMARK OFFICE
CERTIFICATE OF CORRECTION

| | | |
|---|---|---|
| PATENT NO. | : 9,498,315 B2 | Page 1 of 1 |
| APPLICATION NO. | : 14/031056 | |
| DATED | : November 22, 2016 | |
| INVENTOR(S) | : Adams et al. | |

It is certified that error appears in the above-identified patent and that said Letters Patent is hereby corrected as shown below:

On the Title Page

In Item (72), under "Inventors", in Column 1, Line 1, delete "John" and insert -- John M. --, therefor.

Signed and Sealed this
Eighteenth Day of April, 2017

Michelle K. Lee
*Director of the United States Patent and Trademark Office*